US012007380B2

(12) United States Patent
Vrebos et al.

(10) Patent No.: US 12,007,380 B2
(45) Date of Patent: Jun. 11, 2024

(54) APPARATUS AND METHOD FOR X-RAY FLUORESCENCE ANALYSIS

(71) Applicant: Malvern Panalytical B.V., Almelo (NL)

(72) Inventors: Bruno Vrebos, Almelo (NL); Lieven Kempenaers, Almelo (NL); Youhong Xiao, Almelo (NL)

(73) Assignee: Malvern Panalytical B.V., Almelo (NL)

( * ) Notice: Subject to any disclaimer, the term of this patent is extended or adjusted under 35 U.S.C. 154(b) by 0 days.

(21) Appl. No.: 17/743,930

(22) Filed: May 13, 2022

(65) Prior Publication Data
US 2022/0365008 A1 Nov. 17, 2022

(30) Foreign Application Priority Data
May 14, 2021 (GB) ..................................... 2106959

(51) Int. Cl.
*G01N 23/223* (2006.01)
*G01N 33/28* (2006.01)
(52) U.S. Cl.
CPC ......... *G01N 33/287* (2013.01); *G01N 23/223* (2013.01); *G01N 2223/076* (2013.01);
(Continued)
(58) Field of Classification Search
None
See application file for complete search history.

(56) References Cited

U.S. PATENT DOCUMENTS 7,436,926 B2 * 10/2008 Matoba ................ G01N 23/223
378/45
9,360,440 B2 * 6/2016 Allen ................... G01N 35/085
(Continued)

FOREIGN PATENT DOCUMENTS

CN 103969275 A * 8/2014
EP 2 096 431 A1 9/2009
(Continued)

OTHER PUBLICATIONS

European Search Report in EP Application No. 22173093.0-1001, dated Sep. 2, 2022 (8 pages).

*Primary Examiner* — Thomas R Artman
(74) *Attorney, Agent, or Firm* — Leason Ellis LLP

(57) ABSTRACT

This application relates to apparatus and method for x-ray fluorescence analysis. There is provided an X-ray fluorescence analysis apparatus for analysing a sample, The X-ray fluorescence analysis apparatus comprises an X-ray source, a measurement chamber for holding the sample in air, and an X-ray detector. The X-ray source is arranged to irradiate the sample with a primary X-ray beam, to cause the sample to fluoresce. The X-ray detector is arranged to detect characteristic X-rays emitted by the sample and to determine a measured X-ray intensity associated with the characteristic X-rays. An X-ray filter, which transmits the primary X-ray beam, is arranged between the X-ray source and the sample. The X-ray source comprises an anode of material having an atomic number that is less than 25. The X-ray fluorescence analysis apparatus further comprises a sensor arrangement configured to sense air pressure and air temperature. A processor receives the measured X-ray intensity. The processor also receives air pressure data and air temperature data from the sensor arrangement. The processor is configured to carry out a compensation calculation for adjusting (Continued)

the measured X-ray intensity using the air pressure data and the air temperature data.

13 Claims, 4 Drawing Sheets

(52) U.S. Cl.
CPC ............... *G01N 2223/1016* (2013.01); *G01N 2223/204* (2013.01); *G01N 2223/303* (2013.01); *G01N 2223/313* (2013.01); *G01N 2223/637* (2013.01); *G01N 2223/652* (2013.01)

(56) References Cited

U.S. PATENT DOCUMENTS

| | | | |
|---|---|---|---|
| 2007/0269004 A1 | 11/2007 | Matoba et al. | |
| 2012/0236989 A1 | 9/2012 | Hardman | |
| 2014/0270063 A1* | 9/2014 | Allen | G01N 35/085 378/45 |
| 2022/0365008 A1* | 11/2022 | Vrebos | G01N 23/223 |

FOREIGN PATENT DOCUMENTS

| | | | |
|---|---|---|---|
| JP | H05119000 A * | 5/1993 | |
| JP | H05119000 A | 5/1993 | |
| JP | 2014145617 A * | 8/2014 | |
| WO | 9615442 A1 | 5/1996 | |
| WO | 03/049138 A2 | 6/2003 | |

* cited by examiner

APPARATUS AND METHOD FOR X-RAY FLUORESCENCE ANALYSIS

CROSS-REFERENCE TO RELATED PATENT APPLICATIONS

This application claims the priority from Great Britain application no. 2106959.6, filed May 14, 2021, which is incorporated by reference, as if expressly set forth in its respective entireties herein.

FIELD OF THE INVENTION

The present invention relates to an X-ray fluorescence analysis apparatus and a method of carrying out X-ray fluorescence analysis. In particular, the present invention relates to an X-ray fluorescence analysis apparatus and method for characterising samples comprising trace amounts (e.g. less than 50 mg/kg) of a light element.

BACKGROUND OF THE INVENTION

X-ray fluorescence (XRF) analysis is an elemental analysis technique used to obtain information about the composition of a sample. During XRF analysis, the sample is irradiated with X-rays to cause the sample to fluoresce (i.e. to emit characteristic X-rays). The X-rays emitted by the sample are detected by an X-ray detector. In Energy Dispersive X-ray Fluorescence analysis (ED-XRF), different characteristic X-rays (i.e. emitted X-rays of different energies) can be detected substantially simultaneously. This can help to facilitate convenient and time-efficient analysis.

In general, XRF analysis measurements should be accurate and precise; they should be repeatable (as determined by tests carried out by the same operator with the same apparatus in the same test environment) and reproducible (as determined by independent tests). In order to achieve this, XRF analysis apparatuses must be capable of a high level of analytical performance. This may be particularly important if XRF measurements are required to be compliant with national or international standards. There is a need for cost-effective XRF analysis that can be conveniently carried out. It is desirable to take precise measurements without the need for long measurement times (e.g. in order to maximise throughput). It is also desirable for X-ray analysis apparatuses to be capable of a low limit of detection and a low limit of quantification even with short measurement times.

In some fields, it can be particularly challenging to accomplish reliable, convenient and cost-effective XRF analysis. For example, in some industries, it may be desired to analyse samples (e.g. petroleum and petroleum products or biofuels) to identify and quantify trace amounts of some light elements (i.e. "light" elements are elements with an atomic number, Z, of less than or equal to 18). As previously mentioned, these measurements may be required to comply with national/international standards (for example, the International Standard ISO 13032:2012 "Petroleum products—Determination of low concentration of sulfur in automotive fuels—Energy-dispersive X-ray fluorescence spectrometric method").

While some existing XRF analysis apparatuses are capable of identifying and quantifying trace amounts of light elements, they typically require helium in order to do so. As helium becomes more expensive and difficult to come by, the requirement for helium may compromise cost efficiency and convenience. Additionally, in some cases, helium is considered an undesired auxiliary (it can be inconvenient/expensive to store helium safely e.g. on an oilrig).

It would be desirable to provide an XRF analysis apparatus that is capable of providing economical, convenient and reliable analysis. In particular, it would be desirable to provide an X-ray analysis apparatus that is both cost effective and capable of compliance with International Standard ISO 13032:2012 "Petroleum products—Determination of low concentration of sulfur in automotive fuels—Energy-dispersive X-ray fluorescence spectrometric method".

SUMMARY OF THE INVENTION

According to an aspect of the invention, there is provided an X-ray fluorescence analysis apparatus for analysing a sample, the X-ray fluorescence analysis apparatus comprising:
  a measurement chamber for holding the sample in an air atmosphere;
  an X-ray source arranged to irradiate the sample with a primary X-ray beam, the X-ray source comprising an anode comprising material having an atomic number that is less than 25;
  an X-ray filter arranged between the X-ray source and the sample, wherein the X-ray filter is configured to transmit the primary X-ray beam and to attenuate at least some X-rays having energies between 2 keV and 3 keV;
  an X-ray detector arranged to detect X-rays emitted by the sample, wherein the X-ray detector is configured to determine a measured X-ray intensity and a measured X-ray energy;
  a sensor arrangement configured to measure air pressure and air temperature; and
  a processor configured to:
    receive the measured X-ray intensity;
    receive an air pressure measurement and an air temperature measurement from the sensor arrangement; and
    carry out a compensation calculation for adjusting the measured X-ray intensity using the air pressure measurement and the air temperature measurement.

The sample contains an analyte, which may have an atomic number that is equal to or less than 17. By providing this combination of features, the X-ray fluorescence analysis apparatus can be used to obtain highly reliable results—even when only a small amount of the analyte is present in the sample. At the same time, since the sample is measured in an air atmosphere, the use of helium is avoided. In this way, the X-ray analysis apparatus is more convenient and more cost-effective to use.

The X-ray filter is for attenuating X-rays in an energy range corresponding to the characteristic radiation of the analyte. The sensor arrangement may comprise a single sensor capable of detecting both air pressure and air temperature. Alternatively, the sensor arrangement may comprise an air pressure sensor and a separate air temperature sensor. In some embodiments, the sensor arrangement may comprise multiple air pressure sensors and/or air temperature sensors.

The compensation calculation may comprise calculating a correction factor that represents the effect of the air pressure and the air temperature, at the time of measurement, on the measured X-ray intensity.

The X-ray detector may be configured to determine a plurality of X-ray intensities, each X-ray intensity corresponding to a different X-ray energy, and the processor may be configured to calculate a plurality of corresponding correction factors. The different correction factors may correspond to different XRF emissions, and more particularly to XRF emissions of different elements.

The X-ray source may comprise an X-ray tube that is configured to operate at an X-ray tube power of equal to or less than 20 W.

The inventors have realised that by providing this combination of features, high analytical performance can be achieved even for low-atomic number elements, whilst also using a relatively low power (and thus cost-efficient) X-ray tube. The X-ray tube power is the product of the X-ray tube current and the X-ray tube voltage (i.e. the voltage applied across the cathode and the anode). As the skilled person will understand, X-ray tubes are typically operated within a maximum voltage and a maximum power. X-ray tube voltage at which an X-ray tube is operated determines the maximum current at which the X-ray tube should be operated. In other words, every operating voltage (at the maximum voltage or lower) has a maximum current associated with it. The maximum power of the X-ray tube is limited by design parameters, such as the design and material of the cathode, the material and structure of the anode, and the design of the high-voltage generator. The maximum power of the X-ray tube may be equal to or less than 20 W.

The X-ray filter may have an attenuation of greater than 95% at an X-ray energy of greater than 2 keV and less than 3 keV. The X-ray filter may have an attenuation of greater than 95% at an energy range of between 2.0 keV and 2.9 keV.

The X-ray filter may comprise a filter element for attenuating X-rays, the filter element comprising aluminium and having a thickness of between 10 μm and 25 μm.

The thickness of the X-ray filter may be altered by replacing the filter element.

The anode may comprise vanadium, chromium, titanium or scandium.

The anode may be a solid anode, and may preferably be of vanadium or chromium. Most preferably, the anode may be a vanadium anode. That is, the X-ray source may comprise a vanadium anode.

The X-ray detector may be an energy dispersive X-ray detector.

Energy-dispersive X-ray detectors are capable of detecting X-rays at different energies (i.e. corresponding to different characteristic XRF emissions) substantially simultaneously. The X-ray detector may comprise a pulse processor configured to process voltage pulses. The X-ray detector may be a solid-state processor, and may have a resolution greater than 50 eV and less than 300 eV (e.g. 150 eV).

The X-ray fluorescence analysis apparatus may further comprise a housing, wherein the X-ray source, the measurement chamber, the X-ray detector and the X-ray filter are contained inside the housing.

By providing the sensor arrangement inside the housing, the sensor arrangement is capable of measuring the ambient air pressure and ambient air temperature. In this way, the sensor arrangement provides a measure of the air pressure and air temperature inside the measurement chamber.

According to another aspect of the invention, there is provided a method of carrying out X-ray fluorescence analysis on a sample comprising:

holding the sample in a measurement chamber, in an air atmosphere;

generating a primary X-ray beam, from an anode comprising a material having an atomic number of less than 25, and irradiating the sample with the primary X-ray beam;

using an X-ray filter to attenuate at least some X-rays from the anode having an energy between 2 keV and 3 keV;

sensing an ambient air pressure and an ambient air temperature;

detecting X-rays emitted by the sample; and carrying out a compensation calculation for adjusting the measured X-ray intensity using the air pressure measurement and the air temperature measurement.

The measurement chamber holds the sample in an air atmosphere. Accordingly, the X-ray fluorescence analysis apparatus may be configured such that, during X-ray fluorescence measurements, the amount of helium in the measurement chamber is less than 1% by volume.

The X-ray source may comprise an X-ray tube and the X-rays may be generated by operating the X-ray tube at an X-ray tube power of less than 20 W.

The compensation calculation may comprise calculating a correction factor that represents the effect of the air pressure and the air temperature, at the time of measurement, on the measured X-ray intensity.

The X-ray detector may be configured to determine a plurality of X-ray intensities, each X-ray intensity corresponding to a different energy range, and the processor may be configured to calculate a plurality of corresponding correction factors. The different correction factors may correspond to different XRF emissions, and more particularly to XRF emissions of different elements.

The anode may comprise vanadium, chromium, titanium or scandium and the method may further comprise using an X-ray filter to filter X-rays from the X-ray source by attenuating at least some X-rays having an energy of between 2 keV and 3 keV.

The anode is a solid anode, and is preferably of vanadium or chromium. Most preferably, the anode is a vanadium anode. The X-ray filter comprises a filter element for attenuating X-rays; the filter element may comprise aluminium and may have a thickness of between 10 μm and 25 μm. The X-ray filter may attenuate at least 95% of X-rays having an energy of between 2 keV and 3 keV. Alternatively, the X-ray filter may attenuate at least 95% of X-rays having an energy of between 2.0 keV and 2.9 keV.

The sample may comprise petroleum, a petroleum product or a biofuel and/or wherein the sample comprises an analyte having an atomic number that is equal to or less than 17.

The sample may additionally comprise sulphur, chlorine and/or phosphorous. The amount of sulphur, chlorine and/or phosphorous in the sample may be less than less than 50 mg/kg and preferably less than 10 mg/kg.

BRIEF DESCRIPTION OF THE DRAWINGS

Embodiments of the present invention will now be described, by way of example, with reference to the accompanying drawings, in which.

Figure 1:
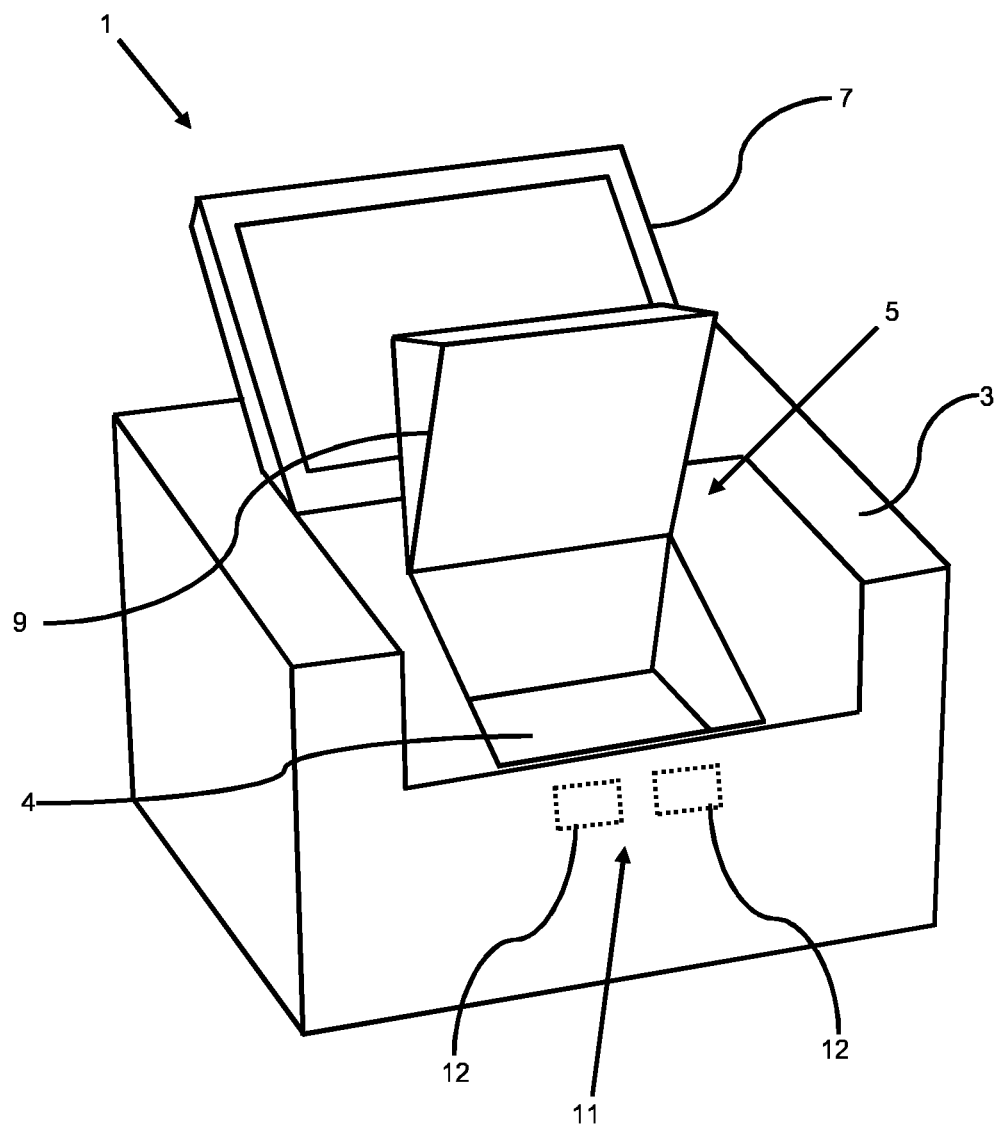
FIG. 1 shows a schematic diagram, in a perspective view, of an X-ray fluorescence analysis apparatus, according to an embodiment.

It should be noted that these figures are diagrammatic and not drawn to scale. Relative dimensions and proportions of parts of these figures have been shown exaggerated or reduced in size, for the sake of clarity and convenience in the drawings.

DETAILED DESCRIPTION

FIG. 1 shows an X-ray fluorescence analysis apparatus 1 according to an embodiment of the invention. The XRF apparatus is a "benchtop" XRF analyser; it comprises a housing 3, which includes a measurement chamber 5 for holding a sample (not shown). The measurement chamber 5 includes a cavity 4 in the interior of the housing 3 and a cover 9. In FIG. 1, the cover 9 is shown in an open configuration for allowing a user to insert the sample into the cavity 4 of the measurement chamber 5. Once the sample has been inserted into the measurement chamber 5, the cover 9 can be moved to a closed configuration in which the cover closes the cavity 4. XRF analysis may subsequently be carried out on the sample.

During XRF analysis, the sample is held in the measurement chamber 5. The X-ray analysis apparatus is capable of achieving high analytical performance without the need for helium or vacuum-sealing of the measurement chamber 5. Accordingly, in embodiments, the atmosphere within the measurement chamber 5 is not controlled: the measurement chamber 5 is not vacuum-sealed and there is no need for helium purging of the measurement chamber. The X-ray fluorescence analysis apparatus may therefore be more cost-efficient and convenient to use.

The X-ray fluorescence analysis apparatus 1 also includes an X-ray source (not shown in FIG. 1), which is positioned inside the housing 3 and arranged to irradiate the sample in the measurement chamber 5. The XRF analysis apparatus is configured to operate the X-ray tube at an X-ray tube power of less than 20 W. Accordingly, the XRF analysis apparatus can achieve high analytical performance with a low power X-ray source.

A sensor arrangement 11 is attached in the interior of the housing 3, close to the measurement chamber. In FIG. 1, the sensor arrangement 11 comprises two sensing elements 12. One of the sensing elements 12 is configured to measure air pressure, and the other sensing element 12 is configured to measure air temperature. The sensing elements are illustrated using dashed lines, to indicate that they are located inside the housing, but outside of the measurement chamber. By measuring the ambient air pressure and ambient air temperature, the sensing elements 12 can be used to estimate the air pressure and air temperature inside the measurement chamber 5. The sensor arrangement is configured to communicate the measured air pressure and air temperature to a processor (not shown in FIG. 1). The processor uses the measured value to carry out environmental compensation, for adjusting X-ray intensity data obtained by the X-ray detector.

As shown in FIG. 1, the X-ray analysis apparatus 1 also comprises a display, for example a touch screen display 7, which is supported by the housing 3. The display 7 may provide access to control inputs, to enable a user to control the X-ray fluorescence analysis apparatus. The display 7 may also be configured to display measurement data (e.g. X-ray intensity data and/or data obtained by the sensor arrangement).

When a sample comprises small amounts of low-atomic number elements, such as sulphur, it is challenging to obtain repeatable and reproducible measurements without controlling the atmosphere within the measurement chamber 5 (i.e. without using a vacuum-sealed measurement chamber or providing helium purging). However, the inventors have found that it is surprisingly possible to achieve high analytical performance by providing an XRF analysis apparatus having a particular combination of incident X-ray components and environmental compensation. In particular, when assessing samples comprising sulphur, it is possible to comply with the repeatability and reproducibility required by International Standard ISO 13032:2012 "Petroleum products—Determination of low concentration of sulfur in automotive fuels—Energy-dispersive X-ray fluorescence spectrometric method".

Figure 2:
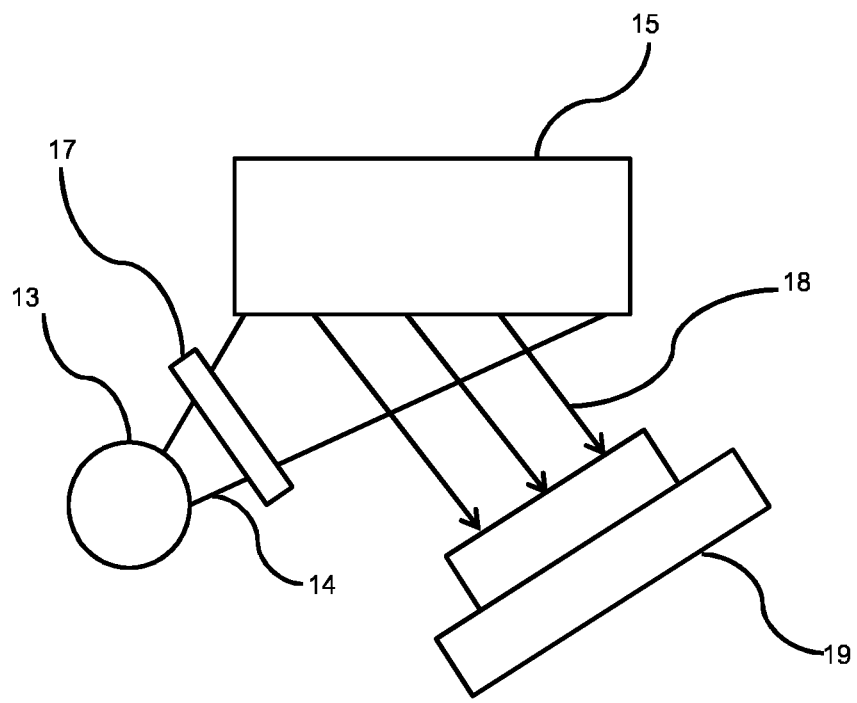
FIG. 2 shows a schematic diagram of the interior of the embodiment of FIG. 1.

FIG. 2 shows part of the interior of the housing of the X-ray fluorescence analysis apparatus 1 of FIG. 1, when a sample 15 is in the measurement chamber. The sample 15 may be, for example, a fuel sample containing a small quantity of a low-atomic number analyte such as sulphur. The X-ray source 13, which is an X-ray tube that is configured to operate at an X-ray tube power of less than 20 W, is arranged to irradiate the sample 15 with X-rays 14. During operation, the X-ray tube emits X-rays for exciting the sample as well as other X-rays (which contribute to background radiation). An X-ray filter 17 is arranged between the sample and the X-ray source, and is configured to significantly attenuate X-rays in an energy range corresponding to characteristic X-rays emitted by the analyte, for example greater than 2 keV and less than 3 keV. The X-ray filter 17 allows the X-rays for exciting the sample to pass with low or no attenuation. An energy-dispersive X-ray detector 19 is arranged to receive characteristic X-rays 18 emitted by the sample 15.

The inventors have found that it is surprisingly possible to analyse samples comprising low-atomic number elements (i.e. elements with atomic numbers 18) whilst achieving high analytical performance, at low cost, and without requiring helium or vacuum sealing. In particular, by providing the combination of the X-ray source, which has an anode of a material with an atomic number that is less than 25, an X-ray filter configured to attenuate X-rays in the range of greater than 2 keV and less than 3 keV and environmental compensation, X-ray fluorescence analysis apparatuses according to embodiments can achieve high repeatability and reproducibility in a convenient and cost-effective way.

In an embodiment, the X-ray source is an X-ray tube comprising a chromium anode and the X-ray filter is an aluminium filter. The thickness of the filter is between 10 µm and 25 µm. For example, the filter may comprise a filter element and a frame for holding the filter element. The filter element has a thickness of between 10 µm and 25 µm, and the frame is capable of holding a filter having any thickness within that range. The filter element can be removed from the frame and replaced with another filter element having a different thickness. Accordingly, the filter element is interchangeable. This combination of incident X-ray components, together with environmental compensation, can achieve high analytical performance for samples containing low amounts (e.g. less than 50 mg/kg) of light elements such as chlorine, sulphur and/or phosphorus, without the use of helium or vacuum-sealing and whilst operating at a low X-ray tube power (e.g. less than 20 W).

In another embodiment, the X-ray source is an X-ray tube comprising a vanadium anode. The X-ray filter is an aluminium filter having a thickness of at least 10 µm. The thickness of the X-ray filter may be altered by replacing the filter element. When the sample is irradiated by primary X-rays from the vanadium anode, it emits fluorescent secondary X-rays. These X-rays are detected by an energy-dispersive X-ray detector 19. This combination of incident X-ray components, together with environmental compensation, can achieve high analytical performance for samples containing small amounts of low-atomic number elements such as chlorine, sulphur and/or phosphorus, without the use of helium or vacuum-sealing and whilst operating at a low X-ray tube power (e.g. less than 20 W). Moreover, this embodiment can achieve high analytical performance even for samples containing very low amounts of sulphur (e.g. less than 10 mg/kg).

Figure 3:
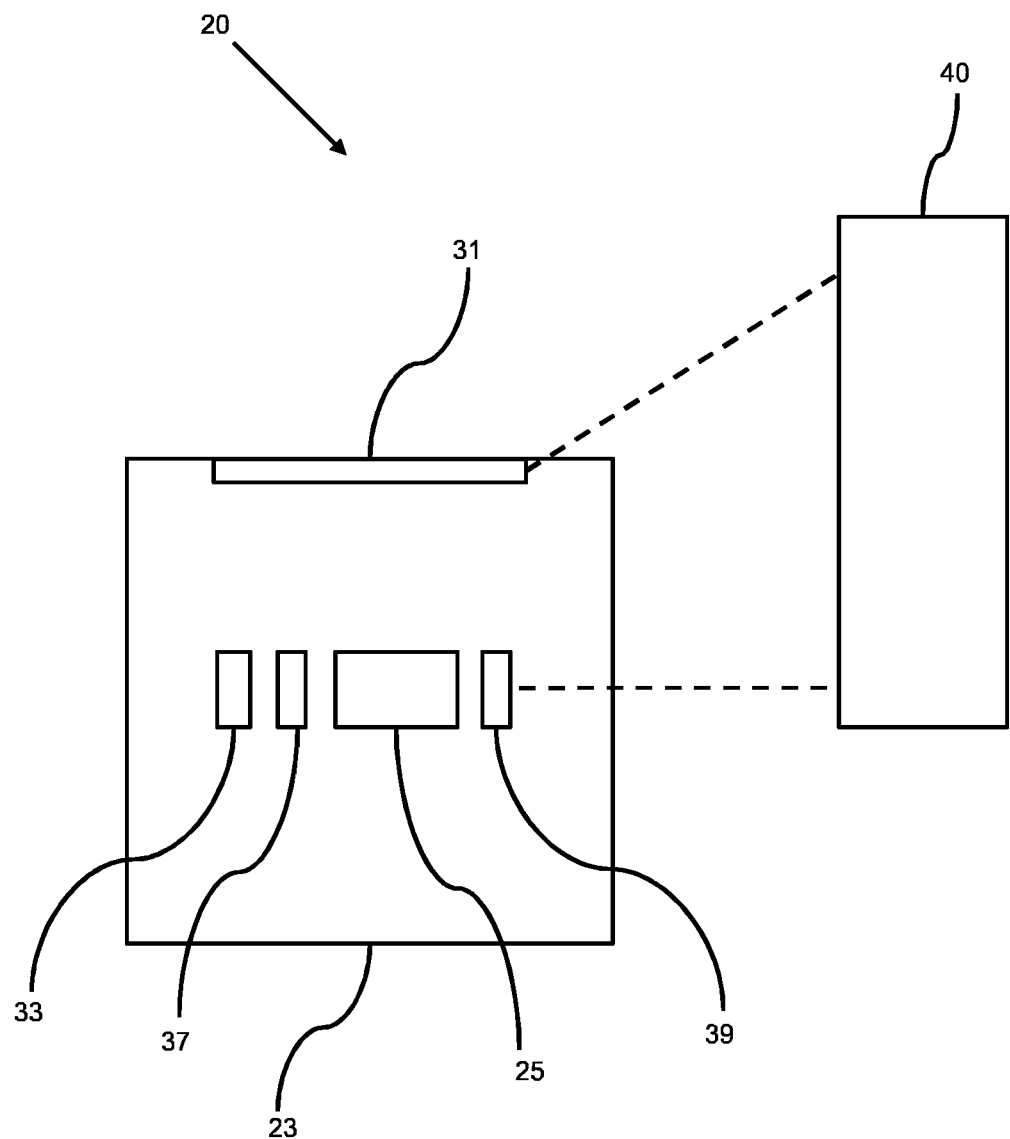
FIG. 3 shows a highly schematic diagram of an X-ray fluorescence analysis apparatus according to an embodiment.

FIG. 3 shows a schematic diagram of an X-ray fluorescence analysis apparatus 20 according to an embodiment of the invention. The X-ray fluorescence analysis apparatus 20 comprises a housing 23, an X-ray source 33, an X-ray detector 39 and a measurement chamber 25 for holding a sample. An X-ray filter 37 is arranged between the X-ray source and the sample. The X-ray filter is configured to attenuate X-rays having energies between 2 keV and 3 keV. The X-ray fluorescence analysis apparatus 20 also comprises a sensor arrangement 31 arranged to sense the ambient air pressure and ambient air temperature inside the housing 23 (and outside of the measurement chamber).

In the embodiment shown in FIG. 3, a processor 40 is located outside of the housing, at a location remote from the housing. However, in some other embodiments, the processor 40 can be located inside the housing. The sensor arrangement 31 and the X-ray detector 39 are in communication with the processor 40 (as illustrated by the dashed lines). The X-ray detector outputs X-ray intensity data to the processor. The sensor arrangement 31 outputs measured air temperature and air pressure values indicative of the air temperature and air pressure inside the measurement chamber at the time the X-ray intensity data was measured. The sensor arrangement 31 communicates the measured air temperature and air pressure values to the processor 40. The communication between the sensor arrangement 31 and the processor 40 may be via a wired connection, or via a wireless connection (e.g. wireless internet, Bluetooth etc.). The processor 40 uses the X-ray intensity data and the air temperature and air pressure data to calculate compensated X-ray intensity values, as will be explained in more detail in connection with FIG. 4.

Figure 4:
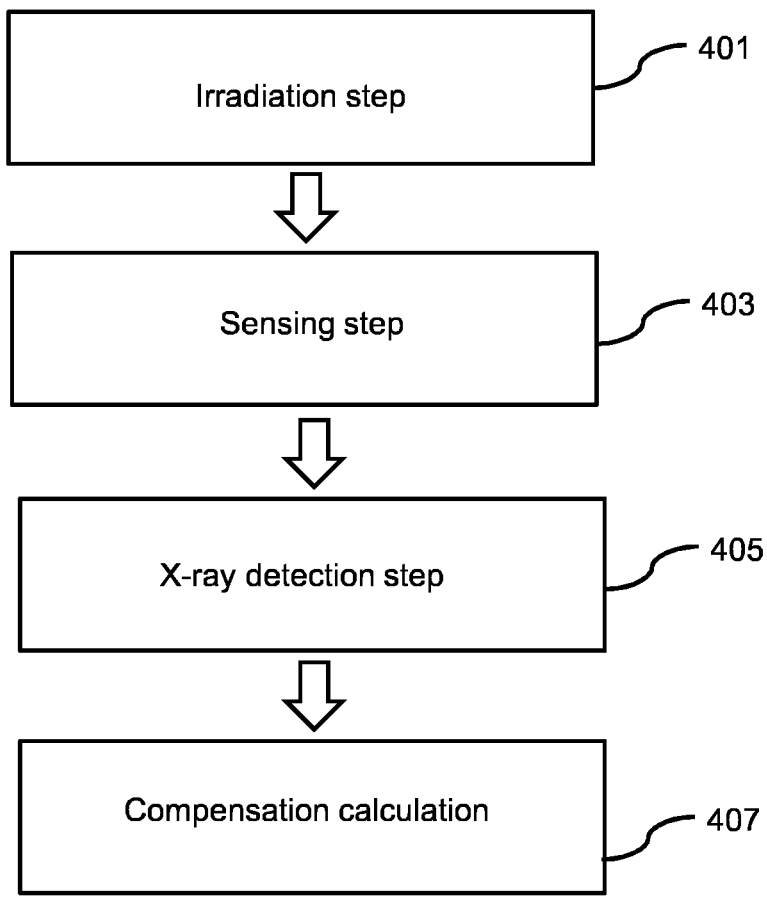
FIG. 4 illustrates a method of X-ray fluorescence analysis according to an embodiment of the invention.

FIG. 4 illustrates a method of X-ray fluorescence analysis according to an embodiment of the invention. Initially, in an irradiation step 401, the sample is placed in a measurement chamber of a benchtop XRF analysis apparatus (e.g. the XRF analysis apparatus described in connection with FIG. 1). An X-ray beam is generated from the X-ray tube, which comprises an anode having an atomic number of less than 25. The X-ray tube is operated at an X-ray tube power of less than 20 W. The sample is then irradiated with X-rays, whilst being held in an air atmosphere (in which the amount of helium in the measurement chamber may be less than 1% by volume).

In a sensing step 403, whilst the sample is being irradiated, the ambient air pressure and ambient air temperature are measured using a sensor arrangement attached to the exterior of the housing of the XRF analysis apparatus. The measured air pressure and air temperature are communicated to a processor.

In an X-ray detection step 405, X-rays emitted by the sample are detected by the X-ray detector as voltage pulses. The X-ray detector communicates the voltage pulses to the processor and the detected voltage pulses are processed, by the processor, to obtain X-ray intensity data (X-ray intensity vs. energy).

Next, in a compensation calculation step 407, the processor carries out a compensation calculation for adjusting the measured X-ray intensity using the air pressure measurement and the air temperature measurement. The compensation calculation determines how the X-ray intensity corresponding to a particular characteristic X-ray is attenuated, and may comprise correcting the X-ray intensity of the characteristic X-ray to take account of the measured air pressure and measured air temperature. For example, the compensation calculation may comprise calculating a correction factor that represents the factor by which the intensity of a characteristic X-rays emitted by the sample in the measurement atmosphere would be attenuated relative to a reference X-ray intensity at the same energy (and at a reference air pressure and air temperature).

In some embodiments, the compensation calculation may comprise determining how the X-ray intensity corresponding to each of a plurality of characteristic X-rays emitted from the sample would be attenuated. For example, a correction factor may be calculated for each of the characteristic X-rays. Further, the compensation calculation may comprise determining how the X-ray intensity of the incident X-ray spectrum and/or background scattering would be attenuated.

It should be understood that various modifications can be made to the illustrated embodiments without departing from the scope of the claims.

Although the embodiment of FIG. 1 has two sensing elements, the X-ray fluorescence analysis apparatus may comprise any number of sensing elements.

Preferably, the sensor arrangement is arranged inside the housing, but outside of the measurement chamber. However, in some embodiments, the sensor arrangement may be provided on the interior of the measurement chamber. In some other embodiments, the sensor arrangement is arranged on an exterior of the housing of the XRF apparatus.

The X-ray filter is preferably an aluminium filter. However, the X-ray filter may alternatively be a silicon-based filter. In some embodiments, the X-ray filter comprises a layer of selenium on a polymer support.

The anode of the X-ray tube may not be vanadium. It may instead be a chromium, titanium or scandium anode. The anode may comprise a combination of vanadium, chromium, titanium and/or scandium The X-ray analysis apparatus may or may not comprise a display. When the X-ray fluorescence analysis apparatus comprises a display, the display may any type of electronic display capable of displaying measurement data. For example, the display be an LCD display or it may be an LED-based display. The display may or may not be a touch screen display.

In some embodiments, the processor is remote from the housing. In other embodiments, the processor may be provided inside the housing. It may be integrated with the X-ray detector, or it may be a separate entity.

The invention claimed is:

1. An X-ray fluorescence analysis apparatus for analysing a sample, the X-ray fluorescence analysis apparatus comprising:
   a measurement chamber for holding the sample in an air atmosphere;
   an X-ray source arranged to irradiate the sample with a primary X-ray beam, the X-ray source comprising an anode comprising material having an atomic number that is less than 25;
   an X-ray filter arranged between the X-ray source and the sample, wherein the X-ray filter is configured to transmit the primary X-ray beam and to attenuate at least some X-rays having energies between 2 keV and 3 keV, wherein the X-ray filter has an attenuation of greater than 95% at an X-ray energy of greater than 2 keV and less than 3 keV, or wherein the filter has an attenuation of greater than 95% at an energy range of between 2.0 keV and 2.9 keV;

an X-ray detector arranged to detect X-rays emitted by the sample, wherein the X-ray detector is configured to determine a measured X-ray intensity and a measured X-ray energy;

a sensor arrangement configured to measure air pressure and air temperature; and a processor configured to:
receive the measured X-ray intensity;
receive an air pressure measurement and an air temperature measurement from the sensor arrangement; and
carry out a compensation calculation for adjusting the measured X-ray intensity using the air pressure measurement and the air temperature measurement.

2. The X-ray fluorescence analysis apparatus of claim 1 wherein the compensation calculation comprises calculating a correction factor that represents the effect of the air pressure and the air temperature, at the time of measurement, on the measured X-ray intensity.

3. The X-ray fluorescence analysis apparatus of claim 1 wherein the X-ray detector is configured to determine a plurality of X-ray intensities, each X-ray intensity corresponding to a different X-ray energy, and the processor is configured to calculate a plurality of corresponding correction factors, wherein each correction factor represents the effect of the air pressure and the air temperature, at the time of measurement, on the measured X-ray intensity.

4. The X-ray fluorescence analysis apparatus of claim 1, wherein the X-ray source comprises an X-ray tube that is configured to operate at an X-ray tube power of equal to or less than 20 W.

5. The X-ray fluorescence analysis apparatus of claim 1, wherein the X-ray filter comprises a filter element for attenuating X-rays, the filter element comprising aluminium and having a thickness of between 10 μm and 25 μm.

6. The X-ray fluorescence analysis apparatus of claim 1, wherein the anode comprises vanadium, chromium, titanium or scandium.

7. The X-ray fluorescence analysis apparatus of claim 5 wherein the X-ray source comprises a vanadium anode.

8. The X-ray fluorescence analysis apparatus of claim 1, wherein the X-ray detector is an energy dispersive X-ray detector.

9. The X-ray fluorescence analysis apparatus of claim 1, further comprising a housing, wherein the X-ray source, the measurement chamber, the X-ray detector and the X-ray filter are contained inside the housing.

10. A method of carrying out X-ray fluorescence analysis on a sample comprising:
holding the sample in a measurement chamber, in an air atmosphere;
generating a primary X-ray beam, from an anode comprising a material having an atomic number of less than 25, and irradiating the sample with the primary X-ray beam;
using an X-ray filter to attenuate at least some X-rays from the anode having an energy between 2 keV and 3 keV, wherein the X-ray filter has an attenuation of greater than 95% at an X-ray energy of greater than 2 keV and less than 3 keV, or wherein the filter has an attenuation of greater than 95% at an energy range of between 2.0 keV and 2.9 keV;
sensing an ambient air pressure and an ambient air temperature;
detecting X-rays emitted by the sample; and
carrying out a compensation calculation for adjusting the measured X-ray intensity using the air pressure measurement and the air temperature measurement.

11. The method of claim 10 wherein the X-ray source comprises an X-ray tube and the X-rays are generated by operating the X-ray tube at an X-ray tube power of less than 20 W.

12. The method of claim 10 wherein the compensation calculation comprises calculating a correction factor that represents the effect of the air pressure and the air temperature, at the time of measurement, on the measured X-ray intensity.

13. The method of claim 10, wherein the sample comprises petroleum, a petroleum product or a biofuel and/or wherein the sample comprises an analyte having an atomic number that is equal to or less than 17.

* * * * *